United States Patent

Mori et al.

[11] 4,296,036
[45] Oct. 20, 1981

[54] SELECTIVE METHOD FOR THE PREPARATION OF INSECT PHEROMONE

[75] Inventors: Kenji Mori, Tokyo; Mitsuru Sasaki, Toyonaka, both of Japan

[73] Assignee: Sumitomo Chemical Company, Limited, Osaka, Japan

[21] Appl. No.: 135,274

[22] Filed: Mar. 31, 1980

[30] Foreign Application Priority Data

Apr. 6, 1979 [JP] Japan .................................. 54-42138

[51] Int. Cl.³ .................. C07D 319/04; C07D 305/14
[52] U.S. Cl. ............................ 260/340.7; 260/343.21;
560/256; 564/253; 568/374
[58] Field of Search .............. 260/340.7, 340.3, 343.21

[56] References Cited

U.S. PATENT DOCUMENTS 3,852,330  12/1974  Jurfluh et al. .................... 260/340.7

OTHER PUBLICATIONS

MacConnell et al., J. Chem. Ecol., 1977, vol. 3, No. 5, pp. 549-551.
Mori et al., Tetrahedron Letters, No. 15, pp. 1329-1332 (1979).
Manuscript of the 22nd Discussion of Natural Organic Compounds, pp. 259-266 (1976).

*Primary Examiner*—Ethel G. Love
*Attorney, Agent, or Firm*—Stevens, Davis, Miller & Mosher

[57] ABSTRACT

A method for the preparation of 3,3,7-trimethyl-2,9-dioxatricyclo[3.3.1.0⁴,⁷]nonane (lineatin, a general name), an aggregation pheromone of an ambrosia beetle, represented by the formula (I),

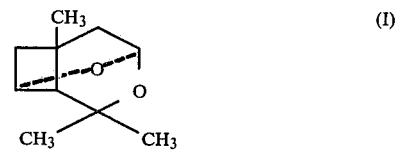

which comprises reacting a keto lactone represented by the formula (II),

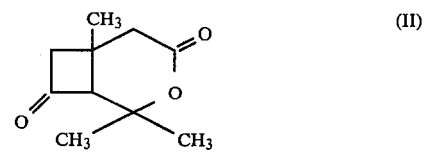

with diisobutylaluminum hydride and subsequently, treating with an acid; and a method for the preparation of said keto lactone represented by the above formula (II), which comprises oxidizing a hydroxy lactone represented by the formula (III),

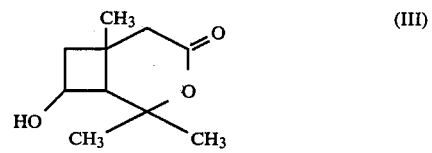

with chromic acid.

4 Claims, No Drawings

SELECTIVE METHOD FOR THE PREPARATION OF INSECT PHEROMONE

This invention relates to a method for preparing 3,3,7-trimethyl-2,9-dioxatricyclo[3.3.1.0^4,7]nonane (lineatin, a general name; hereinafter the term "lineatin" is used) which is an aggregation pheromone of an ambrosia beetle and represented by the formula (I),

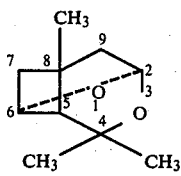

and to a method for preparing 1,5,5-trimethyl-4-oxabicyclo[4.2.0]octa-3,7-dione which is the key intermediate for the preparation of lineatin and represented by the formula (II)

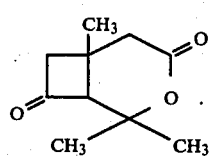

Because of powerful attractant properties toward insects, insect pheromones have recently been used in agriculture and forestry for controlling insect pest populations. However, the quantity of the pheromone obtainable from the natural source is extremely limited; individual insects contain only nano-gram amounts of pheromone. Therefore, the development of a practical chemical synthesis is necessary to supply sufficient amounts of pheromone and to aid in successful pest control.

Lineatin, the subject compound of this invention, is an attractant compound isolated from frass produced by female beetles of *Trypodendron lineatum* (Olivier) boring in Douglas fir. Its chemical structure has been proposed by Silverstein et al. to be one of the two isomeric tricyclic acetals, (I) or (I'). [Journal of the Chemical Ecology, Vol. 3, p. 549 (1977)].

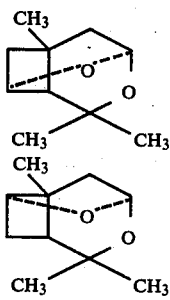

The present inventors have already synthesized both compounds represented by the formulas (I) and (I') through a different route from that of this invention, establishing the structure of lineatin as (I). (Tetrahedron Letters, 1979, No. 15, page 1329). In order to develop a selective route to (I), the present inventors further undertook synthetic studies on lineatin (I) and found a novel method for the preparation of lineatin of the formula (I).

The keto lactone (II) which is the key intermediate for this invention is prepared in a conventional manner illustrated by Scheme (A).

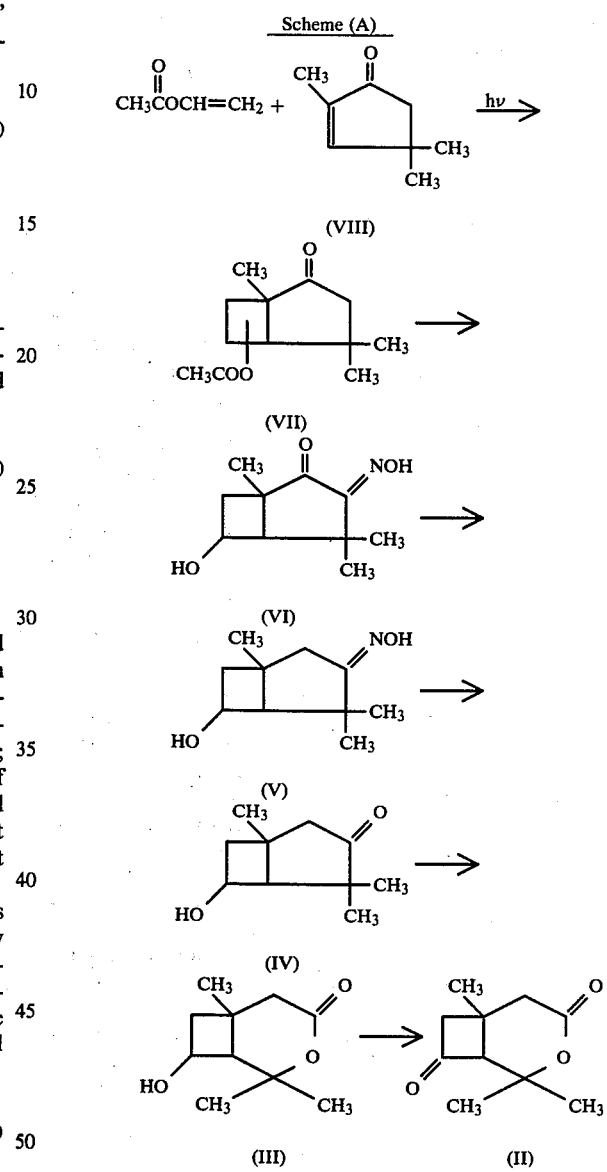

The initial step of the synthesis is the photocycloaddition of vinyl acetate to a cyclopentenone (VIII). The cyclopentenone (VIII) is a known compound simply prepared by heating isobutyl methacrylate in polyphosphoric acid. (Journal of the Chemical Society, Perkin I, 1979, p. 294). The photo-adduct (VII) in benzene is treated with isoamyl nitrite in the presence of potassium tertiary-amylate to give a keto-oxime (VI).

The Wolff-Kisher reduction of (VI) with potassium hydroxide and hydrazine in ethylene glycol gives a crystalline oxime (V). The oxime (V) is treated with titanium trichloride aqueous solution to yield a hydroxy ketone (IV). The hydroxy ketone (IV) is treated with m-chloroperbenzoic acid in the presence of sodium bicarbonate to effect Baeyer-Villiger oxidation giving a hydroxy lactone (III). Reduction of this lactone (III)

with diisobutylaluminum hydride did not yield lineatin (I). This means the OH group in III, IV, V and VI is in exo-configuration. The configuration of the OH group is therefore inverted by first oxidizing the hydroxy lactone (III) to a keto lactone (II) and subsequently reducing (II) with diisobutylaluminum hydride to the desired endo-hydroxy lactol. For this purpose, the hydroxy lactone (III) is converted to the keto lactone (II), the key intermediate of this invention, according to the procedure as described below. To a solution of hydroxy lactone (III) in a solvent such as acetone, methylene chloride (or the like) is added an oxidizing agent such as chromic acid-sulfuric acid, pyridinium chlorochromate, pyridinium dichromate (or the like). Collins reagent (chromic acid-pyridine complex) is also used for the oxidation of (III). The range of the reaction temperature is 0° C. (ice-cooled) to 20° C. (room temperature). The reaction time is from a moment up to 2 hours. The molar ratio of hydroxy lactone (III) to the oxidizing agent is 1 to 1-3. Further, if necessary, a small amount of isopropyl alcohol is added to the reaction mixture to destroy the excess oxidizing agent. The reaction mixture is extracted with a low-boiling solvent such as methylene chloride or ether. The extract is washed with an aqueous sodium chloride solution, then dried and evaporated. The residue is purified by column chromatography. Evaporation of the solvent gives the keto lactone (II), the key intermediate of this invention.

In order to accomplish this invention, the keto lactone (II) is converted to lineatin (I), the subject compound of this invention, according to the procedure as described below. To a solution of keto lactone (II) in a solvent is added dropwise a solution of diisobutylaluminum hydride in n-hexane. The solvents used are ether, n-hexane or the like. The range of the reaction temperature is $-70°$ C. to $+20°$ C. and the reaction time is from a moment up to one hour. The molar ratio of the keto lactone (II) to diisobutylaluminum hydride is 1 to 2-3. After addition of 5-30% hydrochloric acid solution, the reaction mixture is stirred for one hour at room temperature and extracted with a low boiling solvent such as n-pentane. The extract is washed with an alkaline solution and water and distilled to give the intended compound, lineatin (I).

As described above, a primary feature of this invention is that the intended lineatin (I) or the keto lactone (II) can be selectively synthesized from quite inexpensive vinyl acetate and isobutyl methacrylate.

The invention is illustrated below with reference to Examples and Reference Examples.

REFERENCE EXAMPLE 1

Synthesis of (6,7)-acetoxy-1,4,4-trimethylbicyclo[3.2.0]heptan-2-one (VII):

A solution of 25 g of cyclopentenone (VIII) and 250 g of vinyl acetate in 90 ml of benzene was irradiated for 50 hours by a high-pressure mercury-arc lamp (450 W). The solution was then concentrated and distilled to give 11.0 g of a fraction boiling between 92° to 98° C./0.5 mmHg ($n_D^{20}$ 1.4620), (VII).

Elementary analysis:

|  | C % | H % |
|---|---|---|
| Calculated for $C_{12}H_{18}O_3$ | 68.52 | 8.64 |
| Found | 68.27 | 8.71 |

REFERENCE EXAMPLE 2

Synthesis of 3-oximino-6-hydroxy-1,4,4-trimethylbicyclo[3.2.0]heptan-2-one (VI):

To a solution of 1.2 g of potassium tertiary amylate in 20 ml of benzene, while being cooled in ice was added a solution of 1.0 g of the compound (VII) in 2 ml of benzene. After stirring for 30 minutes, 0.57 g of isoamyl nitrite was added to the solution, whereby the solution turned reddish purple. After having been stirred for 36 hours at room temperature, the solution was acidified with 1 N hydrochloric acid. The organic layer was separated, washed with saturated aqueous sodium bicarbonate solution, then with saturated aqueous sodium chloride solution, dried over magnesium sulfate, and concentrated in vacuo to give a brown oil. This oil was purified by silica-gel column chromatography to give 261 mg of crystalline compound (VI), melting at 115°-118° C.

Elementary analysis:

|  | C % | H % | N % |
|---|---|---|---|
| Calculated for $C_{10}H_{15}NO_3$ | 60.88 | 7.68 | 7.04 |
| Found | 60.90 | 8.22 | 6.81 |

REFERENCE EXAMPLE 3

Synthesis of 3-oximino-1,4,4-trimethyl-6-hydroxybicyclo[3.2.0]heptane (V):

To a solution of 2050 mg of the ketoxime (VI) in 25 ml of ethylene glycol, was added 0.7 ml of 80% hydrazine hydrate. After having been kept at 40° to 50° C. for 30 minutes, the solution was admixed with 750 mg of potassium hydroxide and kept at 150° C. for 4 hours under an argon atmosphere. After cooling and adding 50 ml of water, the solution was neutralized with 1 N HCl and extracted with methylene chloride. The extract was washed with an aqueous sodium bicarbonate solution, then with an aqueous sodium chloride solution, dried over magnesium sulfate, and concentrated in vacuo to give 970 mg of a crystalline compound (V). M.p. 130°-133° C.; MS m/e: 183 (M+).

REFERENCE EXAMPLE 4

Synthesis of 1,4,4-trimethyl-6-hydroxybicyclo[3.2.0]heptan-3-one (IV):

To a solution of 600 mg of the oxime (V) in a mixture of 10 ml of dimethoxyethane and 5 ml of water, was added 6 ml of 16% titanium trichloride and the mixture was kept at 50° to 60° C. for 30 minutes under an argon atmosphere. After cooling, the mixture was admixed with 20 ml of water and extracted with methylene chloride. The extract was washed with an aqueous sodium bicarbonate solution, then with an aqueous sodium chloride solution, dried over magnesium sulfate, and concentrated in vacuo to give 425 mg of an oil. This oil was chromatographed over silica gel to give 305 mg of an oil (IV): $n_D^{20}$ 1.4787; MS: m/e 168 (M+).

REFERENCE EXAMPLE 5

Synthesis of 1,5,5-trimethyl-7-hydroxy-4-oxabicyclo[4.2.0]octan-3-one (III):

To a solution of 400 mg of the hydroxyketone (IV) in 8 ml of methylene chloride, while being cooled in ice, were added 770 mg of m-chloroperbenzoic acid and 480 mg of sodium hydrogencarbonate. The mixture was stirred overnight at room temperature and then treated with 10 ml of 10% sodium thiosulfate solution. The aqueous layer was separated and extracted three time with methylene chloride. The combined methylene chloride layer was washed with saturated aqueous sodium bicarbonate solution, then with an aqueous sodium chloride solution, dried over magnesium sulfate, and concentrated in vacuo to give 415 mg of a colorless oil (III); $n_D^{20}$ 1.4845; MS: m/e 169 (M+—CH$_3$), 166 (M+—H$_2$O).

EXAMPLE 1

Synthesis of 1,5,5-trimethyl-4-oxabicyclo-[4.2.0]octa-3,7-dione (II):

(1-a). To a solution of 410 mg of the hydroxy lactone (III) in 10 ml of acetone, while being cooled in ice, was added 0.6 ml of a 8 N chromic acid-sulfuric acid mixture. After 10 minutes, three drops of isopropyl alcohol were added and the mixture was stirred for an additional 30 minutes. The mixture was admixed with 10 ml of methylene chloride and 10 ml of water and allowed to separate into two layers. The aqueous layer was extracted once with methylene chloride. The combined extract was washed with an aqueous sodium chloride solution, dried over magnesium sulfate, and evaporated in vacuo to give 342 mg of an oil. $n_D^{20}$ 1.4837; MS: m/e 182 (M+).

(1-b). To a solution of 300 mg of the hydroxy lactone (III) in 5 ml of methylene chloride, while being cooled in ice, was added 1.0 g of pyridinium chlorochromate. After stirring for 10 minutes at room temperature, 30 ml of ether was added to the mixture and the resulting mixture was fed to the top of a column packed with Florisil. The column was developed with 50 ml of ether and the effluent was concentrated to obtain 270 mg of the compound (II) as a colorless oil.

(1-c). To a solution of 550 mg of the hydroxy lactone (III) in 5 ml of methylene chloride, while being cooled with ice, was added 1.0 g of pyridinium dichromate. After stirring for one hour at room temperature, the mixture was admixed with 30 ml of ether and subsequent work up as described for (1-b) gave 470 mg of the compound (II).

(1-d). To a Collins' reagent prepared from 5 ml of pyridine and 0.5 g of chromic acid, was added at room temperature 200 mg of the hydroxy lactone (III). After stirring for 10 minutes, the mixture was admixed with 30 ml of ether and subsequent work up gave 165 mg of the compound (II).

EXAMPLE 2

Synthesis of 3,3,7-trimethyl-2,9-dioxatricyclo-[3.3.1.0$^{4,7}$]nonane, lineatin (I):

(2-a). Diisobutylaluminum hydride (25% in n-hexane, 2.1 ml) was added to a stirred and cooled (−70° C.) solution of 300 mg of (II) in 3 ml of dry ether under argon atmosphere. After stirring for 40 minutes at −70° C. to −50° C., 5 ml of 1 N hydrochloric acid was added to the mixture. The mixture was gradually warmed to room temperature, followed by addition of 0.6 ml of 6 N hydrochloric acid and the stirring was continued for 1 hour at room temperature. The mixture was diluted with n-pentane. The n-pentane layer was successively washed with aqueous sodium chloride solution, aqueous sodium bicarbonate solution and sodium chloride solution, dried over magnesium sulfate and concentrated under atmospheric pressure to give a crude oil (110 mg). This oil was distilled to give 56 mg of pure lineatin (I); b.p. 120° C.-130° C. (bath temperature)/60 mmHg;

$n_D^{20}$ 1.4625; MS: m/e 168 (M+). Its infrared and nuclear magnetic resonance spectra were identical with those of the natural substance reported by Silverstein et al.

(2-b). Diisobutylaluminum hydride (25% in n-hexane 1.7 ml) was added to a stirred and cooled (−70° C.) solution of 250 mg of (II) in 3 ml of n-hexane under argon atmosphere. The mixture was gradually warmed to 20° C. over a period of one hour followed by addition of 3 ml of 1 N hydrochloric acid and the stirring was continued for 30 minutes at 20° C. One ml of 30% hydrochloric acid was added to the mixture and the stirring was continued for 30 minutes. The mixture was diluted with n-pentane and subsequent work up as described for (2-a) gave 62 mg of lineatin (I).

3. A method for the preparation of a compound represented by the formula (II) according to claim 2, wherein the chromic acid is chromic acid-sulfuric acid, chromic acid-pyridine complex, pyridinium chlorochromate, or pyridinium dichromate.
4. 1,5,5-trimethyl-4-oxabicyclo[4.2.0]octa-3,7-dione represented by the formula (II),
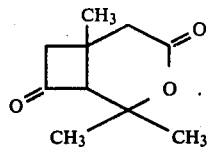

What is claimed is:

1. A method for the preparation of 3,3,7-trimethyl-2,9-dioxatricyclo[3.3.1.0$^{4,7}$]nonane represented by the formula (I),

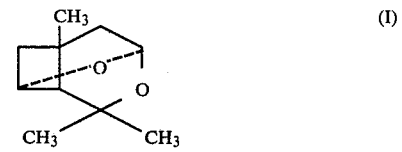

which comprises reacting a keto lactone represented by the formula (II),

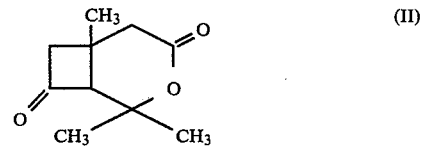

with diisobutylaluminum hydride and subsequently treating with an acid, wherein the reaction temperature is from −70° C. to +20° C., wherein the reaction time is from a moment up to one hour and wherein the molar ratio of the compound represented by the formula (II) to diisobutylaluminum hydride is 1:2-3.

2. A method for the preparation of a keto lactone represented by the formula (II),

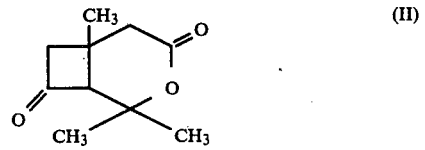

which comprises oxidizing a hydroxy lactone represented by the formula (III),

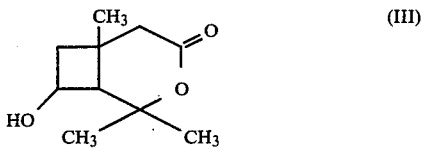

with a chromic acid at 0° to 20° C. from a moment up to two hours, wherein the molar ratio of the compound represented by the formula (III) to the chromic acid is 1:1-3 equivalents.